United States Patent [19]

George et al.

[11] 4,392,858
[45] Jul. 12, 1983

[54] WOUND DRAINAGE DEVICE

[75] Inventors: Robert D. George, Lake St. Louis; Georgio di Palma, St. Peters, both of Mo.

[73] Assignee: Sherwood Medical Company, St. Louis, Mo.

[21] Appl. No.: 283,702

[22] Filed: Jul. 16, 1981

[51] Int. Cl.³ .............................................. A61M 1/00
[52] U.S. Cl. .................................. 604/187; 604/212; 604/213; 604/126
[58] Field of Search .............................. 128/274–278, 128/760, 765–767, 770, DIG. 24; 224/252, 253, 255; 604/187, 212, 213

[56] References Cited

U.S. PATENT DOCUMENTS

| D. 242,652 | 12/1976 | Kunkle, Jr. | 128/DIG. 24 |
|---|---|---|---|
| 2,594,621 | 4/1952 | Derrick | 128/278 |
| 2,655,152 | 10/1953 | Turner et al. | 128/766 |
| 2,815,025 | 12/1957 | Fenton et al. | 128/275 |
| 3,463,159 | 8/1969 | Heimlich | 128/350 |
| 3,683,894 | 8/1972 | Villari | 128/275 |
| 3,779,243 | 12/1973 | Tussey et al. | 128/278 |
| 3,908,664 | 9/1975 | Loseff | 128/350 R |
| 3,945,392 | 3/1976 | Deaton et al. | 137/205 |
| 3,967,645 | 7/1976 | Gregory | 128/274 |
| 4,006,745 | 2/1977 | Sorenson et al. | 128/214 R |
| 4,018,224 | 4/1977 | Kurtz et al. | 128/276 |
| 4,073,294 | 2/1978 | Stanley et al. | 128/278 |
| 4,188,989 | 2/1980 | Anderson | 128/275 |
| 4,265,243 | 5/1981 | Taylor | 128/767 |

FOREIGN PATENT DOCUMENTS 2039745 8/1980 United Kingdom .

OTHER PUBLICATIONS

Publication—Astra Meditec—"Active drainage in a closed system"—drevac (six pages).

Primary Examiner—Richard J. Apley
Assistant Examiner—J. L. Kruter
Attorney, Agent, or Firm—William R. O'Meara; Stanley N. Garber

[57] ABSTRACT

A wound drainage device is provided which includes a manually operable suction pump having inlet and outlet ports, and a pliable fluid storage bag having a pair of plastic sheets in face-to-face contact and an inlet. The pump inlet port is adapted to be connected to a wound suction catheter for removing drainage fluid from the wound. The pump outlet port is connectable to storage bag inlet for discharging drainage fluid into the storage bag without disconnecting the suction catheter. The bag has an upper foldable portion between the main storage portion and the bag inlet to close fluid communication to the bag and can serve as an added protection against drainage fluid flowing back to the suction pump. The storage bag can be used to receive drainage fluid and thereby provide a relatively large storage capacity without requiring a relatively large suction pump.

19 Claims, 4 Drawing Figures

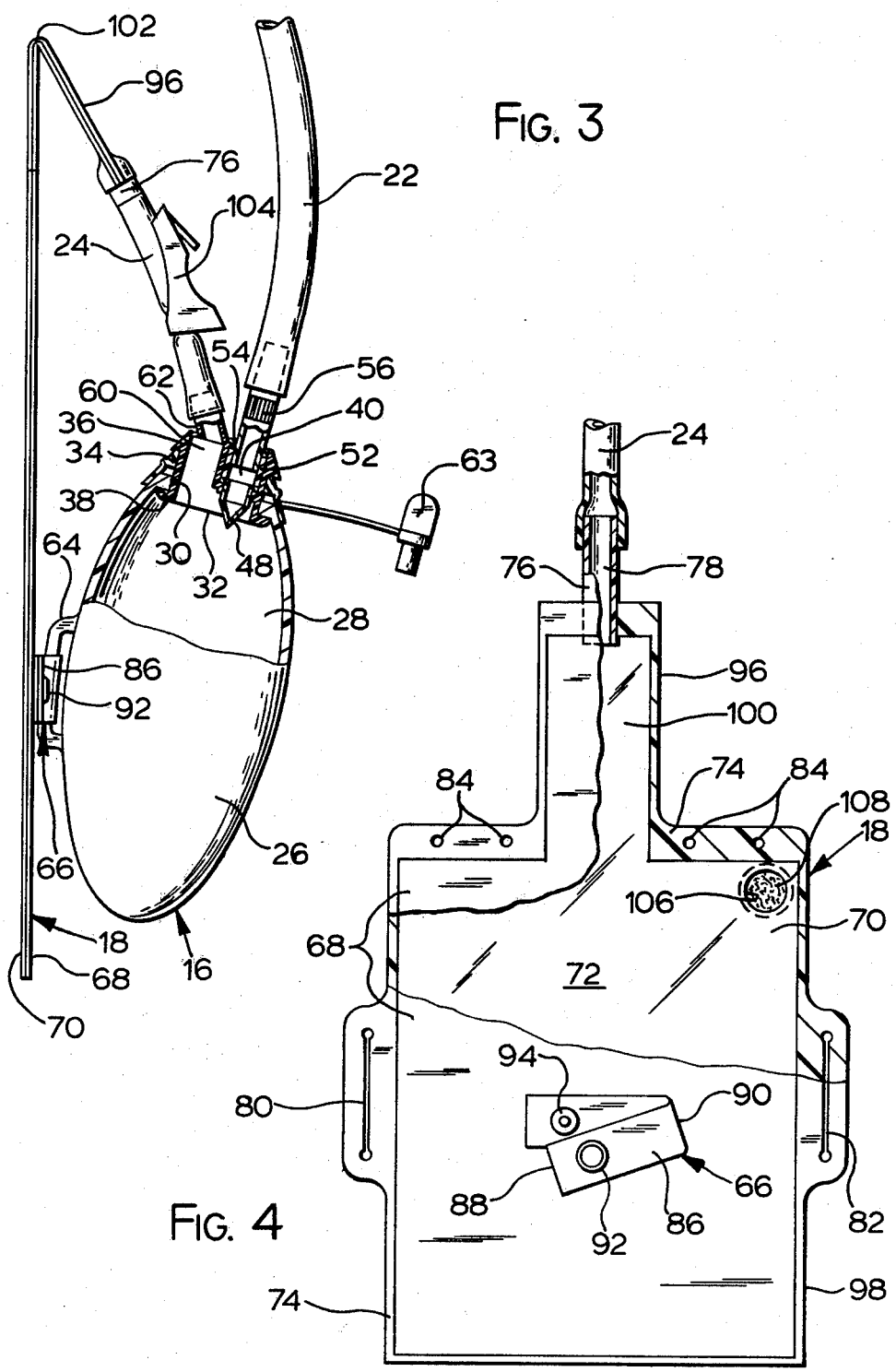

WOUND DRAINAGE DEVICE

DESCRIPTION

1. Technical Field

This invention relates to wound drainage devices and more particularly to wound drainage devices employing auxiliary drainage collection containers.

2. Background Art

Various types of wound suction pumps are used to collect drainage fluids from body wounds, such as surgical wounds, in order to promote healing. In many cases, a manually operated suction pump having a collapsible drainage fluid collection chamber is connected to a suction catheter. After being collapsed, the collection chamber expands effecting a negative pressure for promoting the flow of drainage fluid from the wound to the chamber.

In many cases, a relatively small amount of drainage fluid is expected to be collected so that a relatively small, lightweight, and inexpensive suction pump, such as of the bellows or resilient squeeze bulb type may be used. Because potentially more fluid may be collected than expected or that can be held by the device, auxiliary or storage containers have been used. Collected fluid is discharged from the pump into the auxiliary container without opening the drainage system to ambient air and adversely affecting the sterility of the system. However, apparatus of this type has had certain drawbacks or problems. For example, the pump and container have generally required additional supporting apparatus for the storage container and relatively long connecting tubes between the pump and container. This has increased the cost of the apparatus and, where the apparatus is to be attached to ambulatory patients, the apparatus has been rather complicated to attach, bulky, and parts of the apparatus tend to interfere with the patient's freedom of movement.

DISCLOSURE OF THE INVENTION

It is therefore an object of the present invention to provide an improved wound drainage device having a suction pump, and a storage container for receiving collected drainage fluid from the pump which is compact, highly effective, relatively economical and simple to use, and which substantially overcomes one or more of the above-mentioned problems of the prior art.

In accordance with one aspect of the present invention, a wound drainage device is provided which includes a suction pump for receiving drainage fluid from a body wound and a storage container adapted to receive drainage fluid from the pump. Releasable connection means are provided to connect the pump and storage container in side-by-side relation. In accordance with another aspect, a pliable storage container for receiving drainage fluid from the pump includes a main storage portion and a portion between the main storage portion and an inlet to the container. The portion between the main storage portion and the inlet being folded to close fluid communication between the main storage portion and the inlet when the pump and container are connected together.

These, as well as other objects and advantages of the present invention will become more apparent from the following detailed description and accompanying drawing.

BRIEF DESCRIPTION OF THE DRAWING

FIG. 3 is a side elevational view on an enlarged scale of the device of FIG. 1 with portions broken away and in cross-section; and FIG. 4 is a front elevational view on an enlarged scale of the storage bag of FIG. 1 but on a smaller scale than in FIG. 3, and with portions broken away and in cross-section.

DETAILED DESCRIPTION OF THE PREFERRED EMBODIMENT

Figure 1:
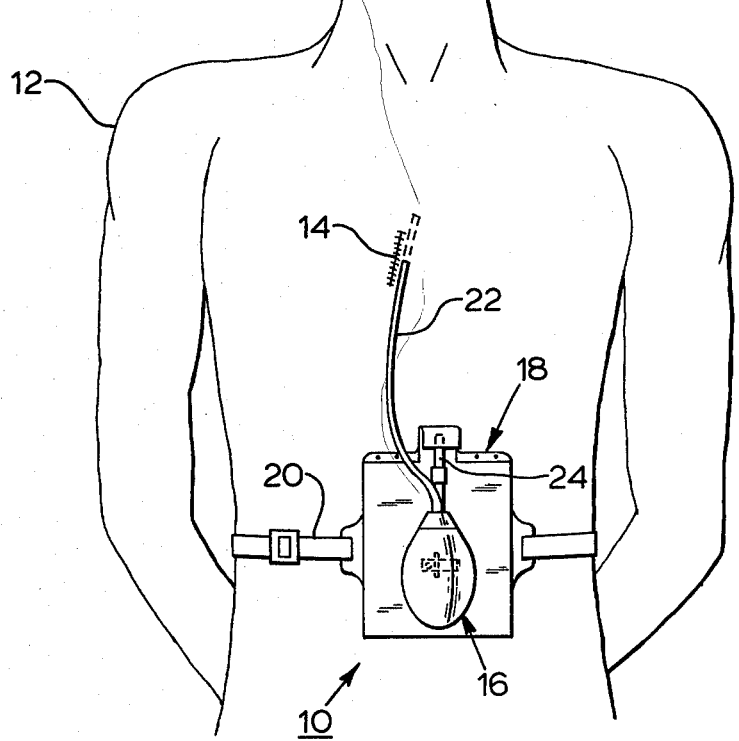
FIG. 1 is a front elevational view of a wound drainage device in accordance with a preferred embodiment of the invention and which is shown connected to a human body.

Referring now to the drawing and particularly to FIG. 1, a wound drainage device 10 is shown attached to a patient, indicated at 12, for removing and collecting wound drainage fluid from a body wound 14. The wound may be, for example, the result of surgery.

The wound drainage device 10 includes a suction pump 16 connected to an auxiliary or storage container 18 which is connected to the patient 12 by means of a removable belt 20 positioned about the patient. A suction catheter 22 has one end disposed within the patient adjacent the body wound 14 and the other end connected to the pump 16 for transferring the wound drainage fluid to the pump. Drainage fluid collected in the pump 16 can be transferred when desired from the pump to the storage container 18 through a tube 24 without disconnecting the suction catheter 22, tube 24, or otherwise breaking the sterility of the drainage fluid system, as will be more fully discussed hereafter.

Figure 2:
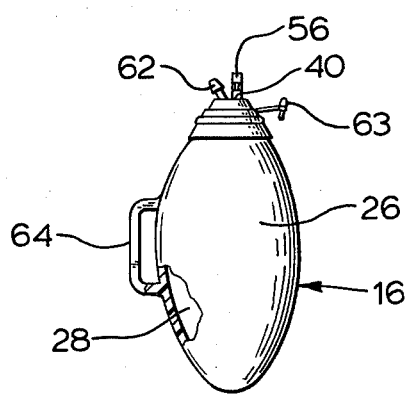
FIG. 2 is a side elevational view on an enlarged scale of the suction pump of the device of FIG. 1.

Referring also to FIGS. 2 and 3, the suction pump 16 is shown including a resilient collapsible container or receptacle illustrated as a resilient squeeze bulb 26 having a collapsible chamber 28. The bulb 26 may be grasped in one hand and squeezed to collapse the walls and chamber 28. When the hand pressure or compressive force is released, the resiliency of the sidewalls of the bulb return the bulb to its predetermined normal or molded shape illustrated in the drawings. When the bulb is released from the collapsed condition, the chamber 28, of course, expands causing a negative pressure or partial vacuum in the chamber. The bulb 26 may be formed of any well known or suitable material used in making squeeze bulbs, for example, rubber, such as a silicone rubber, or a suitable resilient synthetic plastic.

The bulb 26 is closed at the bottom and has an opening 30 at the top in which is disposed an adaptor 32 secured in fluid tight sealing engagement with the upper end of the bulb by a locking ring 34. The adaptor 32 has a pair of integral spaced flanges 36 and 38 between which the upper end of the bulb adjacent opening 30 and the locking ring 34 are forced into resilient tight fitting engagement.

The adaptor 32 has an inlet 40 providing a drainage fluid inlet port for the pump 16. A valve 48, shown as a conventional one-way duck-bill valve has an upper annular flange clamped against a shoulder in the inlet port by an inlet port sleeve 52. The valve 48 may be made of a suitable rubber composition. The valve 48 is arranged to allow fluid to flow from catheter 22 to the bulb chamber 28 but fluid cannot flow from chamber 28 to the catheter even if pressure is inadvertently applied to the bulb 26. A lock ring 54 engaging and the upper end of the sleeve may be used to hold or assist in holding the sleeve 52 in place. The ring 54 may be secured by welding or adhesive where desired.

The sleeve 52 has an inner tapered bore, such as a Luer tapered bore, for frictional sealing engagement with a removable tube or, as shown, a tube adapter 56 which has an external tapered portion that is frictionally connected to catheter 22 so that the catheter is in fluid communication with the bulb chamber 28.

The adapter 32, locking ring 34, sleeve 52, and lock ring 54 may be made of a suitable plastic such as polypropylene.

The adaptor 32 also includes an outlet 60 providing a drainage fluid discharge or outlet port including a tube connector 62 extending outwardly of the bulb at the top for sealingly receiving the bottom end of drainage discharge tube 24. The outlet port 60 connects tube 24 in fluid communication with pump chamber 28. A closure plug 63, integrally connected to the locking ring 34, may be used to close the outlet port 60 after the bulb 26 has been filled with drainage fluid and is disconnected from the catheter 22 for transportation and disposal.

The suction pump 16 is provided with a connector 64 shown as an integrally formed strap or loop on the outer surface of the sidewall of bulb 26. The strap 64 is C-shaped with its ends integrally connected to the bulb sidewall to provide a closed loop with the sidewall. The connector strap 64 is shown in FIG. 3 connected to the storage container 18 by means of a connector 66, to be discussed hereafter, on the outer surface of the sidewall of the storage container so that the pump 16 and container 18 are connected together in assembled relation.

The storage container 18, as best seen in FIG. 4, includes a pair of panels or sheets 68 and 70 connected together to form a pliable bag. These sheets are of somewhat resilient, pliable material, such as a suitable rubber or plastic material, for example, polyvinyl chloride or the like. When the bag 18 is empty, as in the drawings, the sheets 68 and 70 preferably have their inner sides in flat face-to-face relation over substantially their entire surfaces. When fluid enters bag 18, the sheets move away from each other providing a storage chamber indicated at 72. The sheets 68 and 70 are shown welded together by a weld 74 along the entire outer periphery of the bag including around a tube connector 76. Connection 76 has a lumen 78 providing an inlet for the storage bag 18. Connector 76, which may be a piece of plastic tubing, and which is shown connected to the tube 24.

The storage bag 18 has a pair of belt slots 80 and 82 for receiving the patient's belt 20 (FIG. 1). The bag also has a plurality holes 84 near the top which may be used to hang the bag from a support, such as a part of a hospital bed. Attached to the outer side of the front sheet 68 or sidewall of the bag is the connector 66 for releasably connecting the squeeze bulb 16 to the bag in side-by-side relation as shown in FIGS. 1 and 3.

The connector 66 includes a strap 86 having a free end 88 and a fixed end 90 secured to the sheet 68. The strap 86 may be of a suitable plastic such as that of the bag. A releasable coupler shown as a conventional snap fastener has a female snap element 92 fixed to the strap 86 adjacent the free end 88 and a male snap element 94 fixed to the sheet 68 to receive the snap element 92 when the strap connector 66 is closed. When closed, the connector 66 forms a closed loop with the bag which encircles the pump 16 connector loop 64, as seen in FIG. 3, to secure the pump and bag 18 together in side-by-side relation. The connector 66 is shown in the form of a single strap having the complementary fastening elements 92 and 94 at the ends and with a portion of the strap secured such as by welding or an adhesive to the outside surface of the bag sidewall or sheet 68 of the storage bag 18. In assembling the pump bulb 26 to the storage bag 18, the strap 86 is inserted through loop 64 of the bulb and then the fastening elements 92 and 94 are snapped together. The fastening elements, of course, will be snapped apart for removal of the loop 64 to allow the pump bulb 26 to be separated from bag 18.

The storage bag 18 has an upper portion or neck 96 shown extending upwardly from the main body portion, indicated at 98, of the bag. Neck 96 is formed by upper portions of sheets 68 and 70 which form a neck passage 100 connected with the main body chamber 72. The inlet port tube 76 is sealingly connected to the upper end of the neck and fluid flowing into the inlet port 78 flows through neck passage 100 to chamber 72 in the main body portion 98.

When the pump 16 and storage bag 18 are connected together as in FIG. 3, the upper or neck portion 96 of the bag is folded downwardly back toward the bag. The neck is shown folded at or near the middle such as at a fold area or line 102. When folded in this manner, the neck passage 100 is closed, that is, there is no fluid communication between the inlet port 78 and the storage chamber 72.

The length of tube 24 is preferably chosen such that when its opposite ends are connected between the bag inlet tube 76 and the pump outlet tube 62, the neck 96 of the bag is folded to close the neck passage 100. A manually controlled valve or clamp, shown as a conventional tube clamp 104, is used to manually selectively open and close the lumen of tube 24. When the clamp 104 is closing tube 24, fluid communication is cut off between the storage bag inlet 76 and the bulb chamber 28.

When employing device 10, the suction pump bulb 26 may first be attached to the storage bag 18 by the connector strap 86, and the tube 24, closed by clamp 104, attached at its upper end to the bag inlet tube 76. The assembled device 10 may also be attached to the patient's belt 20. With the catheter 22 inserted in the patient and with its lower end connected to the inlet port connector 56, the bulb 26 is hand squeezed to collapse the resilient sidewalls and chamber 28 of the bulb and discharge air from the bulb through the open outlet port 60 to the atmosphere. With the bulb collapsed, the closed tube 24 is connected to the outlet connector 62. Under these conditions, the catheter connects the wound in fluid communication with the bulb chamber 28, which chamber is tending to expand and effect a negative pressure or partial vacuum in the bulb and wound. This negative pressure facilitates the flow of drainage fluid from the wound to the bulb chamber.

If desired, the bulb 26 and storage bag 18 may be completely connected to the patient as in FIG. 1 except for connecting the bulb 26 to the bag 18 by means of strap 86. With the bulb 26 held above the bag 18 so that the neck 96 is unfolded or straight, and with the clamp 104 released, the bulb can be squeezed to discharge air into the bag 18. The clamp can then be closed while the bulb is collapsed. This will effect a negative pressure in the bulb while it is connected to the catheter to initiate the flow of fluid from the wound. The valve 48 will prevent air flow to the patient.

If it is desired to discharge collected drainage fluid from the bulb 26 to the storage bag 18, for example, in order to remove more drainage fluid than can be collected in the bulb, the bulb 26 may be first removed from the bag 18 by opening the snap fastening elements 92 and 94. The bulb 26 is removed from the bag 18 without disconnecting the bulb from the catheter 22 or tube 24. The bulb may then be raised above the bag which tends to straighten the bag neck 96 to permit fluid flow through the neck. The tube clamp 104 is released to open tube 24. The bulb is then squeezed to discharge collected drainage fluid from the bulb chamber 28, through the bulb outlet 62, tube 24, inlet 78, and neck 96, and to the storage chamber 72 of bag 18. This drainage fluid causes the chamber 72 to expand.

During the discharge of drainage fluid from the bulb 26 to the bag 18, the one-way valve 48 prevents fluid from flowing from the bulb chamber 28 into the catheter and patient since the valve 48 is in the series flow path between the bulb chamber and catheter or patient.

After a desired amount of fluid has been transferred to the storage bag, the valve or tube clamp 104 is actuated to close tube 24 and the compression forces collapsing the bulb are now released. This automatically reestablishes the negative pressure in bulb chamber 28 so that suction draining of fluid from the wound can continue. Fluid cannot flow back from the bag 18 to the bulb because of closed clamp 104. The bulb 26 may then be reconnected in side-by-side relation with the bag as in FIG. 3.

The above procedure of transfering collected drainage fluid from the pump 16 to the storage bag 18 may be repeated until the storage bag is full.

The folded neck 96 of the storage bag in device 10 serves as a back-up or security valve for the valve or tube clamp 104. For example, even if the clamp 104 is not fully closed or inadvertently opened fluid collected in the bag is prevented by the folded neck from flowing back into the bulb even though the bulb is producing a suction force for removing fluid from the patient.

The foldable upper portion or neck 96 is a manually controlled fluid valve which is open to allow fluid flow from the pump 16 to the storage bag 18 when the neck is substantially straight and closed when folded as in FIG. 3 to prevent flow between the bag and pump. In some cases, the foldable neck may be used without a valve or clamp 104.

Since device 10 has the pump bulb 26 and storage bag 18 connected together in side-by-side relation or with their sidewalls laterally adjacent each other, the device is compact and provides a relatively large fluid holding capacity for its overall volume. The device 10 is well suited for ambulatory patients because of its compactness, and because it can be made of light weight plastic materials. The bag 18 supports the pump and is of pliable plastic and serves as a backing pad for the pump when worn by the patient. Also, the supporting means for the device 10 is relatively simple since only the bag 18 need be directly connected to the patient or other apparatus because the sidewall of pump 16 is connected to the sidewall of the bag 18.

In some cases, it is desired to provide the storage container 18 with a gas or air vent to allow air to escape from the container. Such an air vent may be provided by forming an opening 106 (FIG. 3) in an upper corner of a sidewall, such as in sheet 70, of the container, and covering it with a filter, such as a hydrophobic sheet member 108. With an air vent, air that may be initially in the container 18 or which is pumped into it when placing the device 10 in use or during the transfer of drainage fluid from the pump 16 to the container, can discharge from the bag to the atmosphere. In this way, even though air is introduced into the container 18, it will not adversely affect the liquid capacity of the container. Being hydrophobic, filter 108 will allow gas to pass through to the atmosphere but will not allow liquid to pass through it.

Filter 108 may be made, for example, of a material known under the trademark "Tyvek" produced by E.I. duPont de Nemours and Company, Inc. of Wilmington, Delaware. "Tyvek" sheet is believed to be a spunbonded olefin and a network of minute polyethylene fibers made by an integrated spinning and bonding process in which a random distribution of continuous polyethylene fibers are self-bonded by heat and pressure. Other suitable hydrophobic filters may be used. For example, an "Acropor" filter made of acrylonitrile polyvinyl chloride reinforced with nylon may be used in some cases. The "Acropor" filter may be obtained from Gelman Instrument Company 600 South Wagner Road, Ann Arbor, Michigan. The periphery of filter 108 may be connected to the container by adhesive or other suitable means.

As various changes could be made in the above construction without departing from the scope of the invention, it is intended that all matter contained in the above description and apparatus shown in the accompanying drawing shall be interpreted as illustrative and not in a limiting sense.

We claim:

1. A patient wound drainage device comprising manually operable wound suction pump means for connection with a catheter disposed adjacent a body wound of a patient for removing and collecting drainage liquid from the body wound, said pump means including a resilient, at least partially collapsible drainage receptacle, a pump inlet port connected to said receptacle means for connection said pump inlet port to a catheter so that said receptacle can receive drainage liquid from the body wound, and a pump outlet port connected to said receptacle for discharging drainage liquid therefrom, said receptacle being hand squeezable and releasable for producing a suction force at said pump inlet port, a one-way valve connected in series with said pump inlet port to prevent drainage liquid flow from said receptacle to the catheter, a fluid drainage storage bag including a pair of pliable sheet material members in face-to-face relation forming the sidewalls of the bag, a bag inlet port connected to the upper end portion of said bag, fluid connector means for connecting said pump outlet port with said bag inlet so that drainage liquid can be pumped from said receptacle into said bag by hand squeezing said receptacle, releasable connection means for connecting said receptacle to said bag in side-by-side relation with the sidewalls of said bag and receptacle in facing adjacent relation and with said receptacle between the upper and lower ends of said bag, and means for securing said bag, with said receptacle connected thereto, to the patient.

2. The device of claim 1 wherein said connection means includes first connector means on the exterior of the sidewall of said bag, and second connector means on the exterior of the sidewall of said receptacle, said second connector means being releasably connectable with said first connector means.

3. The device of claim 2 wherein one of said first and second connector means includes a strap having one end connected to one of said sidewalls and a releasable locking member for connecting the opposite end of said strap to said one sidewall, and the other of said first and second connector means includes a loop connected to the other of said sidewalls for receiving said strap.

4. The device of claim 3 wherein said strap is connected to the sidewall of said bag, and said loop is connected to the sidewall of said receptacle.

5. The device of claim 1 or 2 wherein said receptacle comprises a resilient squeeze bulb of plastic material.

6. The device of claim 1, 2, 3 or 4 wherein said storage bag includes a main fluid storage portion and a foldable portion between said storage portion and said inlet port, said foldable portion being folded when said receptacle and bag are connected together in side-by-side relation to close fluid communication between said inlet port and said main portion.

7. The device of claim 1 wherein facing sides of said sheets are in flatwise facing relation and in contact with each other over substantially their entire surface when said bag is empty of drainage fluid.

8. The device of claim 1 wherein said bag has a main storage portion and a neck portion of less width than between said inlet port and said main storage portion, said neck portion being foldable when said receptacle and bag are connected together in side-by-side relation to close fluid communication between said inlet port and said main storage portion.

9. The device of claim 8 wherein said receptacle is a plastic hand-squeezable resilient squeeze bulb.

10. The device of claim 1 further including a tube connectable between said inlet port of said storage bag and said outlet of said receptacle, and valve means connected in series between said bag and said receptacle outlet to prevent fluid flow from said bag to said receptacle.

11. The device of claim 10 further including a releasable tube closure member adapted to close said tube to prevent drainage fluid flow from said storage bag to said receptacle during drainage flow from a body wound to said receptacle.

12. The device of claim 1 further including manually operable valve means connected to prevent fluid flow from said bag to said receptacle.

13. The device of claim 12 wherein said valve means comprises a foldable portion of said storage bag.

14. A patient wound drainage device comprising a hand squeezable wound suction pump including a resilient, at least partially collapsible receptacle means having an upper end portion, an inlet port connected to said upper end portion for connection with a suction catheter adapted to be placed in fluid communication with a body wound of a patient, said receptacle means being hand squeezable and releasable for producing a suction force for facilitating drainage liquid flow from the wound to said receptacle means, a one-way fluid valve connected in series with said inlet port and said receptacle means to prevent return drainage liquid flow from said receptacle means to the catheter, a drainage fluid outlet port connected to said receptacle means, a pliable drainage fluid storage bag including a pair of sheet members of pliable material in face-to-face relation with each other forming the sidewalls of the bag, said bag having a main storage portion and an upper neck portion having one end connected to said main storage portion, and a bag inlet port connected to the other end of said neck portion, and tube means connected between said bag inlet port and said receptacle means fluid outlet port, means for removably connecting said receptacle means to said bag with said neck portion folded back toward said main storage portion to close off fluid communication between said bag inlet port and said main storage portiion, said neck portion being substantially unfoldable to allow drainage liquid flow from said receptacle means through said tube means, said neck portion and to said bag when said said receptacle means is removed from said bag and moved to substantially unfold said neck portion and squeezed to cause drainage liquid to flow therefrom, and means for securing said bag with said receptacle means connected thereto to the patient.

15. The device of claim 14 wherein said receptacle means fluid outlet port is in said upper end portion of said receptacle means.

16. The device of claim 14 further including manually releasable closure means connected in series between said receptacle means fluid outlet port and said bag inlet port.

17. The device of claim 14 including releasable connection means connecting said receptacle means and said bag in side-by-side relation with said receptacle means between the upper and lower ends of said bag.

18. The device of claim 14 wherein gas vent means are connected to said storage bag to allow gas to flow from said bag to the atmosphere.

19. The device of claim 18 wherein said vent means comprises an opening in the sidewall of said bag and an hydrophobic filter member covering said opening.

* * * * *